US007462491B2

(12) United States Patent
Thompson

(10) Patent No.: US 7,462,491 B2
(45) Date of Patent: *Dec. 9, 2008

(54) METHODS AND COMPOSITIONS FOR DIAGNOSIS AND MONITORING OF PROSTATE CANCER PROGRESSION BY DETECTION OF SERUM CAVEOLIN

(75) Inventor: Timothy C. Thompson, Houston, TX (US)

(73) Assignee: Baylor College of Medicine, Houston, TX (US)

( * ) Notice: Subject to any disclaimer, the term of this patent is extended or adjusted under 35 U.S.C. 154(b) by 411 days.

This patent is subject to a terminal disclaimer.

(21) Appl. No.: 10/941,747

(22) Filed: Sep. 15, 2004

(65) Prior Publication Data

US 2005/0079562 A1    Apr. 14, 2005

Related U.S. Application Data

(63) Continuation-in-part of application No. 10/355,259, filed on Jan. 31, 2003, now abandoned.

(60) Provisional application No. 60/504,384, filed on Sep. 18, 2003, provisional application No. 60/352,513, filed on Jan. 31, 2002.

(51) Int. Cl.
*G01N 33/48* (2006.01)
*G01N 33/53* (2006.01)
*A61B 5/055* (2006.01)

(52) U.S. Cl. .................... 436/64; 436/518; 436/536; 436/71; 436/813; 435/7.1; 435/7.23; 424/9.34

(58) Field of Classification Search ............... 424/9.34, 424/142.1; 435/7.23, 7.1; 436/64, 518, 536, 436/71, 813
See application file for complete search history.

(56) References Cited

U.S. PATENT DOCUMENTS

| | | | |
|---|---|---|---|
| 4,317,818 A | | 3/1982 | Benson et al. |
| 4,376,110 A * | | 3/1983 | David et al. ................. 435/5 |
| 4,925,835 A | | 5/1990 | Heston |
| 5,116,615 A | | 5/1992 | Gokcen et al. |
| 5,260,224 A | | 11/1993 | Stossel et al. |
| 5,545,807 A * | | 8/1996 | Surani et al. ................ 800/6 |
| 5,633,161 A | | 5/1997 | Shyjan |
| 5,783,182 A | | 7/1998 | Thompson |
| 5,834,234 A | | 11/1998 | Gallo |
| 7,029,859 B2 * | | 4/2006 | Thompson ................. 435/7.1 |
| 2002/0065224 A1 | | 5/2002 | Bender et al. |

FOREIGN PATENT DOCUMENTS

| | | |
|---|---|---|
| WO | WO 86/03226 A1 | 6/1986 |
| WO | WO 94/04196 A1 | 3/1994 |
| WO | WO 94/16737 A2 | 8/1994 |
| WO | WO 94/28129 A2 | 12/1994 |
| WO | WO 95/19369 A1 | 7/1995 |
| WO | WO 96/30389 A1 | 10/1996 |
| WO | WO 97/09055 A1 | 3/1997 |
| WO | WO 97/18454 A2 | 5/1997 |
| WO | WO 99/22773 A2 | 5/1999 |

OTHER PUBLICATIONS

Tahir, S.A., et al. Cancer Res., 61: 3882-3885, 2001.*
Liu, P. et al, Nature Cell Biology, 1: 369-375, 1999.*
Li, W.-P. et al. Journal of Cell Science, 114(7): 1397-1408, 2001.*
Nilsson, BO, et al. Ups. J. Med. Sci. 104(3): 199-206, 1999.*
Perkins, G.L. et al. American Family Physician 68(6): 1075-1082, 2003.*
Gion, M. et al. Anticancer Research 16: 2279-2284, 1996.*
Gretzer, M.B. et al. Urol. Clin. N. Am. 30: 677-686, 2003.*
Anonymous, Proceedings of the American Association for Cancer Research, 36, 266, #1589, Mar. 1995.
Brown et al., "Antigen retrieval in cryostat tissue sections and cultured cells by treatment with sodium dodecyl sulfate (SDS)," Histochem Cell Biol., 105, 261-267, 1996.
Chen et al., "Isolation and characterization of the promoter region of human nm23-H1, a metastasis suppressor gene," Abstract 122: 2406, 1994.
Feron et al., "Endothelial nitric oxide synthase targeting to caveolae," The Journal of Biological Chemistry, 271:37, 22810-22814, Sep. 13, 1996.
Garver et al., "Increased expression of caveolin-1 in heterozygous Niemann-Pick type II human fibroblasts," Biochemical and Biophysical Research Communications, 236, 189-193, 1997.
Morre et al., "Ligand-stimulated B2-adrenergic receptor internalization via the constitutive endocytic pathway into rab5-containing endosomes," Journal of Cell Science, 108, 2983-2991, 1995.
Parton et al., "Caveolin-3 associates with developing t-tubules during muscle differentiation," The Journal of Cell Biology, 136:1, 137-154, Jan. 13, 1997.
Parton, "Ultrastructural localization of gangliosides; GM is concentrated in caveolae," The Journal of Histochemistry and Cytochemistry, 42:2, 155-166, 1994.
Scherer et al., "Caveolin isoforms differ in their N-terminal protein sequence and subcellular distribution," The Journal of Biological Chemistry, 270:27, 16395-16401, Jul. 1995.
Song et al., "Expression of caveolin-3 in skeletal, cardiac, and smooth muscle cells," The Journal of Biological Chemistry, 271:25, 15160-15165, Jun. 21, 1996.
Wu et al., "Clustering of GPI-anchored folate receptor independent of both cross-linking and association with caveolin," The Journal of Membrane Biology, 159: 137-147, 1997.
Aihara et al., "Frequency of apoptotic bodies positively correlates with Gleason grade in prostate cancer," Human Pathology, 25:8, 797-801, Aug. 1994.

(Continued)

*Primary Examiner*—Alana M. Harris
*Assistant Examiner*—Anne L Holleran
(74) *Attorney, Agent, or Firm*—Vinson & Elkins LLP

(57) ABSTRACT

Serum cav-1 is disclosed as a biomarker for prostate cancer that has the power to differentiate between prostate cancer and BPH patients.

7 Claims, 3 Drawing Sheets

OTHER PUBLICATIONS

Aihara et al., "The frequency of apoptosis correlates with the prognosis of Gleason grade 3 adenocarcinoma of the prostate," Cancer, 75:2, 522-529, Jan. 15, 1995.

Bist et al., "Two sterol regulatory element-like sequences mediate up-regulation of caveolin gene transcription in response to low density lipoprotein free cholesterol," Proc. Natl. Acad. Sci. USA, 94, 10693-10698, Sep. 1997.

Block et al., "Isolation of cDNAs that are differentially expressed between androgen-dependent and androgen-independent prostate carcinoma cells using differential display PCR," Prostate, 26:4, 213-224, Apr. 1995.

Boak et al., "Regulation of lysyl oxidase expression in lung fibroblasts by transforming growth factor-B1 and prostaglandin E2," American Journal of Respiratory Cell and Molecular Biology, 11, 751-755, 1994.

Bookstein et al., "p53 is mutated in a subset of advanced-stage prostate cancers," Cancer, 53, 3369-3373, Jul. 19, 1993.

Carter et al., "Prediction of metastatic potential in an animal model of prostate cancer: flow cytometric quantification of cell surface charge," The Journal of Urology, 142, 1338-1341, Nov. 1989.

Chamness et al., "The effect of androgen on nitric oxide synthase in the male reproductive tract of the rat," Fertility and Sterility, 63:5, 1101-1107, May 1995.

Contente et al., "Expression of gene rrg is associated with reversion of NIH 3T3 transformed by LTR-c-H-ras," Science, 249, 796-798, August. 17, 1990.

Danks, "Disorders of copper transport: menkes disease and the occipital horn syndrome," Connective Tissue and Its Heritable Disorders, 487-505, 1993.

Donehower, "Mice deficient for p53 are developmentally normal but susceptible to sponataneous tumours," Nature,356, 215-221, Mar. 19, 1992.

Eastham et al., "In vivo gene therapy with p53 of p21 advenovirus for prostate cancer," Cancer Research, 55, 5151-5155, Nov. 15, 1995.

Eastham et al., "Prostate cancer gene therapy: herpes simplex virus thymidine kinase gene transduction followed by ganciclovir in mouse and human prostate cancer models," Human Gene Therapy, 7, 515-523, Mar. 1, 1996.

Eastham et al., "Transforming growth factor-B1: comparative immunohistochemical localization in human primary and metastatic prostate cancer," Laboratory Investigation, 73:5, 628-635, 1995.

Egawa et al., "Alterations in mRNA levels for growth-related genes after transplantation into castrated hosts in oncogene-induced clonal mouse prostate carcinoma," Molecular Carcinogenesis, 5, 52-61, 1992.

Einstein, "Hormonal therapy for prostate cancer—when to use it," Cancer Control, 32-36, Jan./ Feb. 1995.

Feres-Filho et al., "Pre- and post-translational regulation of lysyl oxidase by transforming factor-B1 in osteoblastic MC3T3-E1 cells," The Journal of Biological Chemistry, 270:51, 30797-30803, Dec. 22, 1995.

Feron et al., "Endothelial nitric oxide synthase targeting to caveolae," The Journal of Biological Chemistry, 271:37, 22810-22814, Sep. 13, 1996.

Fielding et al, "Caveolin mRNA levels are up-regulated by free cholesterol and down-regulated by oxysterols in fibroblast monolayers," Pro. Natl. Acad. Sci. USA, 94, 3753-3758, Apr. 1997.

Fingert et al., "In vivo model for differentiation therapy of leukemia and solid tumors," National Institutes of Health Publication, 84-2635, Serno Symposia Publications from Rven. Press, 277-286, 1984.

Fox et al., "p53 ans c-myc expression in stage A1 prostatic adenocarcinoma: useful prognostic determinants?," The Journal of Urology, 150, 490-494, Aug. 1993.

Garver et al., "Increased expression of caveolin-I in heterozygous Niemann-Pick type II human fibroblasts," Biochemical and Biophysical Research Communications, 236, 189-193, 1997.

Glenney, "Tyrosine phosphorylation of a 22-kDa protein is correlated with transformation by rous sarcoma virus," The Journal of Biological Chemistry, 264:34, 20163-20166, Dec. 5, 1989.

Goltsov et al., "A novel p53-regulated gene encoding a four transmembrane domain in mouse prostate cancer cells," AACR Annual Meeting, Philadelphia, PA, Apr. 10-14, 1999.

Guarini et al., "Transfer of the interleukin-2 gene into human cancer cells induces specific antitumor recognition and restores the expression of CD3/T-cell receptor associated signal transduction molecules," Blood, 89:1, 212-218, Jan. 1, 1997.

Gudas, "Retinoids, retinoid-responsive genes, cell differentiation, and cancer," Cell Growth & Differentiation, 3, 655-662, Sep. 1992.

Hajnal et al., "Up-regulation of lysyl oxidase in spontaneous revertants of H-ras-transformed rat fibroblasts," 4670-4675.

Hall et al., "Adenylate kinase: an oncodevelopmental marker in an animal model for human prostatic cancer," Clin. Chem., 31:10, 1689-1691, 1985.

Hamalainen et al., "Quantitative polymerase chain reaction of lysyl oxidase mRNA in malignantly transformed human cell lines demonstrates that their low lysyl oxidase activity is due to low quantities of its mRNA and low levels of transcription of the respective gene," The Journal of Biological Chemistry, 270:37, 21590-21593, Sep. 15, 1995.

Jourdan-Le Saux et al., "Functional analysis of the lysyl oxidase promoter in myofibroblast-like clones of 3T6 fibroblast," Journal of Cellular Biochemistry, 64, 328-341, 1997.

Kadmon et al., "The role of retinoids in prostate cancer chemoprevention," Poster Session Abstracts, First SPORE Investigators Meeting, Rockville, Maryland, Jul. 18-20, 1993.

Kagan, "Characterization and regulation of lysyl oxidase," Regulation of Matrix Accumulation, 321-398, 1986.

Kagan et al., "Properties and function of lysyl oxidase," Am. J. Respir. Cell Mol. Biol., 5, 206-210, 1991.

Kivirikko, "Collagens and their abnormalities in a wide spectrum of diseases," Annals of Medicine, 25, 113-126, 1993.

Kivirikko et al., "Posttranslational modifications of collagen and their alterations in heritable diseases," 263-292.

Koleske et al., "Reductional of caveolin and caveolae in oncogenically transformed cells," Proc. Natl. Acad. Sci. USA, 92, 1381-1385, Feb. 1995.

Kuivaniemi et al., "Deficient production of lysyl oxidase in cultures of malignantly transformed human cells," FEBS Letters, 195:1,2, 261-264, Jan. 1986.

Li et al., "Sre tyrosine kinases, Ga subunits, a H-ras share a common membrane-anchored scaffolding protein, caveolin," The Journal of Biological Chemistry, 271:46, 29182-29190, 1996.

Liang et al., "Differential display and cloning of messenger RNAs from human breast cancer versus mammary epithelial cells," Cancer Research, 52, 6966-6968, Dec. 15, 1992.

Liang et al., "Differential display of eukaryotic messenger RNA by means of the polymerase chain reaction," Science, 257, 967-971, Aug. 14, 1992.

Macoska et al., "Loss of the 17p chromosomal region in a metastatic carcinoma of the prostate," The Journal of Urology, 147, 1142-1146, Apr. 1992.

Manam et al., "Dose-related changes in the profile of ras mutations in chemically induced CD-1 mouse liver tumors," Carcinogenesis, 16:5, 1113-1119, 1995.

Merz et al., "Elevated Transforming Growth Factor-B1 and B3 mRNA levels are associated with ras + myc-induced carcinomas in reconstituted mouse prostate: evidence for a paracrine role during progression," Molecular Endocrinology, 5:4, 503-513, 1991.

Mokulis et al., "Screening for prostate cancer: pros. cons. and reality," Cancer Control, 15-21, Jan./Feb. 1995.

Moore et al., "Ligand-stimulated B2-adrenergic receptor internalization via the constitutive endocytic pathway into rab5-containing endosomes," Journal of Cell Science, 108, 2983-2991, 1995.

Nasu et al., "Suppression of caveolin expression induces androgen sensitivity in metastatic androgen-insensitive mouse prostate cancer cells," Nature Medicine, 4:9, 1062-1064, Sep. 1998.

Nelson, "Alternatives to death: understanding androgen-independent prostate cancer," Nature Medicine, 4:9, 1011-1012, Sep. 1998.

Neumann, "Entstehung und behandlung von tumoren, immunsuppressiva," Allgemeine und Specielle Pharmakologie and Toxikologie, Edition 5, 1987.

Parton, "Ultrastructural localization of gangliosides; GM is concentrated in caveolae," The Journal of Histochemistry and Cytochemistry, 42:2, 155-166, 1994.

Peyrol et al., "Lysyl oxidase gene expression in the stromal reaction to in situ and invasive ductal breast carcinoma," American Journal of Pathology, 150:2, 497-507, Feb. 1997.

Ren et al., "Identification and characterization of p53 regulated genes in a mouse prostate cancer cell line," AACR Annual Meeting, New Orleans, LA, Mar. 28-Apr. 1, 1998.

Ren et al., "Reduced lysyl oxidase mRNA levels in experimental and human prostate cancer," Cancer Research, 58, 1-6, Mar. 15, 1998.

Sargiacomo et al., "Oligomeric structure of caveolin: implications for caveolae membrane organization," Proc. Natl. Acad. Sci. USA, 92, 9407-9411, Sep. 1995.

Schlag, "Fruherkennung von krebs mit hilfe von molekularbiologischen marken," Onkologie, 18, 2-7, 1995.

Schneider et al., "7,12-dimethylbenz[a]anthracene-induced mouse keratinoyte malignant transformation independent of harvey ras activation," The Journal of Investigative Dermatology, 101:4, 595-599, Oct. 1993.

Sehgal et al., "Transforming growth factor B1 stimulates contrasting responses in metastatic versus primary mouse prostate cancer-derived cell lines in Vitro," Cancer Research, 56, 3359-3365, Jul. 15, 1996.

Shanely et al., "Transforming growth factor-B1 increases lysyl oxidase enzyme activity and mRNA in rat aortic smooth muscle cells," Journal of Vascular Surgery, 446-452, Mar. 1997.

Shimura et al., "Reduction in lysyl oxidase expression is an independent preditor of recurrence following radical prostatectomy," Abstract, American Urological Association 94th Annual Meeting, May 1-6, 1999.

Slawin et al., "Dietary Fenretinide, a synthetic retinoid, decreases the tumor incidence and the tumor mass of ras-+myc-induced carcinomas in the mouse prostate reconstitution model system," Cancer Research, 53, 4461-4465, Oct. 1, 1993.

Slawin et al., "Dietary retinoids decrease the incidence and increase lymphocytic infiltration of ras+myc induced carcinomas in the mouse prostate reconstitution model system," American Urological Association, Inc., Annual Meeting, San Antonio, TX, Oct. 1, 1992.

Stapleton et al., "Primary human prostate cancer cells harboring p53 mutations are clonally expanded in metastases," Clinical Cancer Research, 3, 1389-1397, Aug. 1997.

Taber's Cyclopedic Medical Dictionary, pp. 1207 and 1229, 1993.

Tan et al., "Identification of the lysyl oxidase gene as a target of the antiocogenic transcription factor, IRF-1, and its possible role in tumor suppression," Cancer Research, 56, 2417-2421, May 15, 1996.

Taylor et al., "Evidence for synergistic interactions between ras, myc and mutant form of p53 in cellular transformation and tumor dissemination," Oncogene, 1383-1390, Feb. 10, 1992.

Thompson et al., "Exogenous leukocyte and endogenous elastases can mediate mitogenic activity in pulmonary artery smooth muscle cells by release of extracellular matrix-bound basic fibroblast growth factor," Journal of Cellular Physiology, 166, 495-505, 1996.

Thompson et al., "Caveolin-1: a complex and provocative therapeutic target in prostate cancer and potentially other malignancies," Emerging Therapeutic Targets, 3:2, 337-346, 1999.

Thompson et al., "Caveolin-1, a metastasis-related gene that promotes cell survival in prostate cancer," Apoptosis, 4:4, 233-237, 1999.

Thompson et al., "Genetic predisposition and mesenchymal-epithelial interactions in ras+myc-induced carcinogenesis in reconstituted mouse prostate," Molecular Carcinogenesis, 7, 165-179, 1993.

Thompson et al., "Loss of p53 function leads to metastasis in ras+myc-initiated mouse prostate cancer," Oncogene, 10, 869-897, 1995.

Thompson et al., "Loss of p53 function leads to metastasis in ras+myc-initiated mouse prostate cancer," Abstract for Fogarty International Meeting, Jun. 26-28, 1995.

Thompson, "Metastasis-related genes in prostate cancer: the role of caveolin-1," Cancer and Metastasis, 17, 439-442, 1999.

Thompson et al., "Multistage carcinogenesis induced by ras and myc oncogenes in a reconstituted organ," Cell, 56, 917-930, Mar. 24, 1989.

Thompson et al., "Transforming growth factor B1 as a biomarker for prostate cancer," Journal of Cellular Biochemistry, Supplement 16H, 54-61, 1992.

Thompson et al., "Transgenic models for the study of prostate cancer," Cancer, 71:3, 1165-1171, Feb. 1, 1993.

Truong et al., "Association of transforming growth factor-B1 with prostate cancer," Human Pathology, 24:1, 4-9, Jan. 1993.

Tulchinsky et al., "Transcriptional analysis of the mts1 gene with specific reference to 5' flanking sequences," Proc. Natl. Acad. Sci. USA, 89, 9146-9150, Oct. 1992.

Vater et al., "Native cross-links in collagen fibrils induce resistance to human synovial collagenase," Biochem. J. 181, 639-645, 1979.

Welch et al., "Transforming growth factor B stimulates mammary adenocarcinoma cell invasion and metastatic potential," Proc. Natl. Acad. Sci. USA, 87, 7678-7682, Oct. 1990.

Wood et al., "Sensitivity of immunohistochemistry and polymerase chain reaction in detecting prostate cancer cells in bone marrow," The Journal of Histochemistory and Cytochemistry, 42:4, 505-511, 1994.

Wu et al., "Identification of a human hepatocellular carcinoma-associated tumor suppressor gene by differential display polymerase chain reaction," Life Sciences, 57:11, 1077-1085, 1995.

Xiong et al., "Human D-type cyclin," Cell, 65, 691-699, May 17, 1991.

Yang et al., "Association of caveoline protein with prostate cancer progression," Journal of Urology, 157:4, 446, Abstract #1742, Apr. 1997.

Yang et al., "Elevated expression of caveolin is associated with prostate and breast cancer," Clinical Cancer Research, 4, 1873-1880, Aug. 1998.

Yang et al., "Perineural invasion of prostate carcinoma cells is associated with reduced apoptotic index," Cancer, 78:6, 1267-1271, Sep. 15, 1996.

Lederman et al., "A single amino acid substitution in a common african allele of the CD4 molecule ablates binding of the monoclonal antibody, OKT4," Molecular Immunology, 28:11, 1171-1181, 1991.

Li et al., "B-Endorphin omission analogs: Dissociation of immunoreactivity from other biological activites," Proc. Natl. Acad. Sci. USA, 77:6, 3211-3214, Jun. 1980.

Ngo et al., "Computational complexity, protein structure prediction, and the levinthal paradox," The Protein Folding Problem and Tertiary Structure Prediction, 491-495, 1994.

Patlolla et al., "Overexpression of caveolin-1 in experimental colon adenococarcinomas and human colon cancer cell lines," Oncology Reports, 11, 957-963, 2004.

Racine et al., "Reduction of caveolin 1 gene expression in lung carcinoma cell lines," Biochemical and Biophysical Research Communications, 255, 580-586, 1999.

Sternberg et al., "Caveolin, cholesterol and ras signalling," Nature Cell Biology, 1, E35-E36, 1999.

Williams et al., "The caveolin proteins," Genome Biology, 5:3, 214. 1-214.7, 2004.

Yang et al., "Caveolin-1 expression in clinically confined human prostate cancer: a novel prognostic marker," Cancer Research, 59, 5719-5723, 1999.

* cited by examiner

METHODS AND COMPOSITIONS FOR DIAGNOSIS AND MONITORING OF PROSTATE CANCER PROGRESSION BY DETECTION OF SERUM CAVEOLIN

CROSS-REFERENCE TO RELATED APPLICATIONS

The present application claims priority to U.S. Provisional Patent Application Ser. No. 60/504,384, filed Sep. 18, 2003, and is a continuation-in-part of U.S. patent application Ser. No. 10/355,259, filed Jan. 31, 2003, now abandoned both of which are incorporated herein by reference. U.S. patent application Ser. No. 10/355,259, filed Jan. 31, 2003 claims priority to U.S. Provisional Patent Application Ser. No. 60/352,513, filed Jan. 31, 2002.

REMARKS

The specification of U.S. Ser. No. 10/355,259, which is expressly incorporated by reference in the specification of the present application, contained a priority claim to U.S. Provisional application No. 60/352,513, filed Jan. 31, 2002.

STATEMENT REGARDING FEDERALLY SPONSORED RESEARCH OR DEVELOPMENT

The work which led to the inventions disclosed herein was funded at least in part by grants CA 68814, CA 50588 and SPORE P50-58204 from the National Cancer Institute. The federal government therefore has certain rights in the inventions.

BACKGROUND OF THE INVENTION

Prostate cancer is the second leading cause of death and the most common cancer in men. African-American men have a much higher incidence of and mortality from prostate cancer than White-American men (Greenlee, R. T., Hill-Harmon, M. B., Murray, T., and Thun, M. Cancer statistics, 2001. CA Cancer J Clin, 51: 15-36, 2001). The precise risk factors for prostate cancer are unknown with both genetic factors and environmental factors likely to be involved (Brawley, O. W., Giovannucci, E., and Kramer, B. S. Epidemiology of prostate cancer. In: S. P. Vogelzang N J, Shipley W U, Coffey D S (ed.), Comprehensive Textbook of Genitourinary Oncology, pp. 533-544. Philadelphia, Pa.: Lippincott Williams and Wilkins, 2000). In recent years, efforts to detect and treat prostate cancer have increased dramatically throughout the United States (Greenlee, et al., 2001). The widespread use of serum prostate specific antigen (PSA) based screening of asymptomatic men resulted in a sharp (over two fold) increase in detection of the incidence of prostate cancer during the 1990s. PSA is a member of the human kallikrein family of serine proteases produced by the prostatic epithelium and the epithelial lining of the periurethral glands. Although PSA is selectively expressed in prostate, it is not prostate cancer specific, and serum PSA levels rise not only in prostate cancer, but also in benign prostatic disease, physical trauma to the prostate, and other conditions affecting the integrity of the prostate gland (Stephan, C., Jung, K., Diamandis, E. P., Rittenhouse, H. G., Lein, M., and Loening, S. A. Prostate-specific antigen, its molecular forms, and other kallikrein markers for detection of prostate cancer. Urology, 59: 2-8, 2002). It is therefore not surprising that serum PSA levels lack the specificity to permit the accurate prediction of the pathological or clinical stage (Babaian, R. J., Camps, J. L., Frangos, D. N., Ramirez, E. I., Tenney, D. M., Hassell, J. S., and Fritsche, H. A. Monoclonal prostate-specific antigen in untreated prostate cancer. Relationship to clinical stage and grade. Cancer, 67: 2200-2206, 1991; Partin, A. W., Yoo, J., Carter, H. B., Pearson, J. D., Chan, D. W., Epstein, J. I., and Walsh, P. C. The use of prostate specific antigen, clinical stage and Gleason score to predict pathological stage in men with localized prostate cancer. J Urol, 150: 110-114, 1993). Since the standard treatments for prostate cancer are only useful for localized disease, they are entirely dependent on accurate staging for their effectiveness. Therefore, because of the inadequacies of serum PSA or any other commonly available modality to accurately predict pathological or clinical stage, the curative potential of standard localized treatment is limited. Indeed, over recent years there has emerged a unique and significant patient population who have received localized therapy but who have recurred with a rising serum PSA indicating either local (Partin, et al., 1993) recurrence and/or occult metastasis (Ohori, M., Goad, J. R., Wheeler, T. M., Eastham, J. A., Thompson, T. C., and Scardino, P. T. Can radical prostatectomy alter the progression of poorly differentiated prostate cancer? J Urol, 152: 1843-1849, 1994; Zietman, A. L., Edelstein, R. A., Coen, J. J., Babayan, R. K., and Krane, R. J. Radical prostatectomy for adenocarcinoma of the prostate: the influence of preoperative and pathologic findings on biochemical disease-free outcome. Urology, 43: 828-833, 1994). Additional biomarkers with specificity for virulent prostate cancer and/or metastatic disease are clearly needed.

Caveolin-1 (cav-1) is the principle structural protein of caveolae and functions in signal transduction and lipid transport. Cav-1 can also accumulate in cellular compartments other than the plasma membrane, such as the cytosol of skeletal muscle cells and keratinocytes, in modified mitochondria of airway epithelial cells, and in the secretory pathway of endocrine and exocrine cells (Li, W. P., Liu, P., Pilcher, B. K., and Anderson, R. G. Cell-specific targeting of caveolin-1 to caveolae, secretory vesicles, cytoplasm or mitochondria. J Cell Sci, 114: 1397-1408, 2001). Through biochemical and molecular analysis of prostate cancer tissues and cell lines cav-1 was previously identified as being overexpressed in metastatic prostate cancer (Yang, G., Truong, L. D., Timme, T. L., Ren, C., Wheeler, T. M., Park, S. H., Nasu, Y., Bangma, C. H., Kattan, M. W., Scardino, P. T., and Thompson, T. C. Elevated expression of caveolin is associated with prostate and breast cancer. Clin Cancer Res, 4: 1873-1880, 1998). Cav-1 is also an independent prognostic marker for prostate cancer progression in lymph node negative patients who have recurred following radical prostatectomy (Yang, G., Truong, L. D., Wheeler, T. M., and Thompson, T. C. Caveolin-1 expression in clinically confined human prostate cancer: a novel prognostic marker. Cancer Res, 59: 5719-5723, 1999) and there is a significant association of increased cav-1 in prostate cancer in African-American men vs. White-American men (Yang, G., Addai, J., Ittmann, M., Wheeler, T. M., and Thompson, T. C. Elevated caveolin-1 levels in African-American versus white-American prostate cancer. Clin Cancer Res, 6: 3430-3433, 2000). Additionally, cav-1 upregulation is associated with the development of androgen-insensitive prostate cancer (Nasu, Y., Timme, T. L., Yang, G., Bangma, C. H., Li, L., Ren, C., Park, S. H., DeLeon, M., Wang, J., and Thompson, T. C. Suppression of caveolin expression induces androgen sensitivity in metastatic androgen-insensitive mouse prostate cancer cells. Nat Med, 4: 1062-1064, 1998) and androgen-insensitive prostate cancer cells secrete biologically active cav-1 in a steroid-regulated fashion (Tahir, S. A., Yang, G., Ebara, S., Timme, T. L., Satoh, T., Li, L., Goltsov, A., Ittmann, M., Morrisett, J. D., and Thompson, T. C. Secreted Caveolin-1 24 Stimulates Cell Survival/Clonal Growth and Contributes to Metastasis in Androgen-insensitive Prostate Cancer. Cancer Res, 61: 3882-3885, 2001). The secreted cav-1 can stimulate viability and clonal growth in prostate cancer cells that do not express cav-1 and cav-1 was detected in the serum $HDL_3$ fraction of prostate cancer patients by western blot analysis (Tahir et al., 2001).

SUMMARY

An aspect of the present disclosure is a sensitive, reproducible and specific immunoassay for the measurement of cav-1 in serum. Further provided are methods of detecting and monitoring progress of prostate disease in which cav-1 is significantly elevated in the sera of prostate cancer patients compared to those of subjects with BPH or normal controls.

Caveolin-1 (cav-1), the major protein component of caveolae, plays an important role in multiple signaling pathways, molecular transport and cellular proliferation and differentiation. The specific functions of cav-1/caveolae are highly cell and context dependent. Cav-1 expression is increased in metastatic human prostate cancer, and cav-1 cellular protein expression is predictive of recurrence of the disease following radical prostatectomy. Cav-1 is secreted by androgen-insensitive prostate cancer cells, and can be detected, by western blotting, in the $HDL_3$ fraction of serum specimens from patients with prostate cancer.

Using rabbit polyclonal antibodies with specificity for cav-1 a direct sandwich immunoassay for the determination of cav-1 in serum is disclosed herein. A recombinant human cav-1 fusion protein, over expressed and purified from 293 PE cells was used as a calibrator.

The assay was highly specific and had a minimum detection limit of 0.017 ng/ml (mean+3 SD of zero calibrator) and measuring range of up to 200 ng/ml. Intra-assay CV was 2.29-6.74% and inter-assay CV was 2.81-6.43% over the serum concentration tested 0.04-31.89 ng/ml. The recovery limit of cav-1 by the assay was 89.55-100.28%. The median serum cav-1 level in 102 prostate cancer patients with clinically localized disease (0.463 ng/ml) was significantly higher than 81 healthy control men (0.324 ng/ml, P=0.046, Mann-Whitney test) or 107 men with BPH (0.172 ng/ml, P=0.0317, Mann-Whitney test).

Throughout this disclosure, unless the context dictates otherwise, the word "comprise" or variations such as "comprises" or "comprising," is understood to mean "includes, but is not limited to" such that other elements that are not explicitly mentioned may also be included. Further, unless the context dictates otherwise, use of the term "a" may mean a singular object or element, or it may mean a plurality, or one or more of such objects or elements.

Abbreviations: Cav-1, caveolin-1; PSA, prostate specific antigen; BPH, benign prostatic hyperplasia; BSA, bovine serum albumin; HDL high density lipoprotein; TBS, tris-buffered saline; HRP, horseradish peroxidase; PAGE, polyacrylamide gel electrophoresis; SDS, sodium dodecyl sulphate.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DETAILED DESCRIPTION

Figure 1:
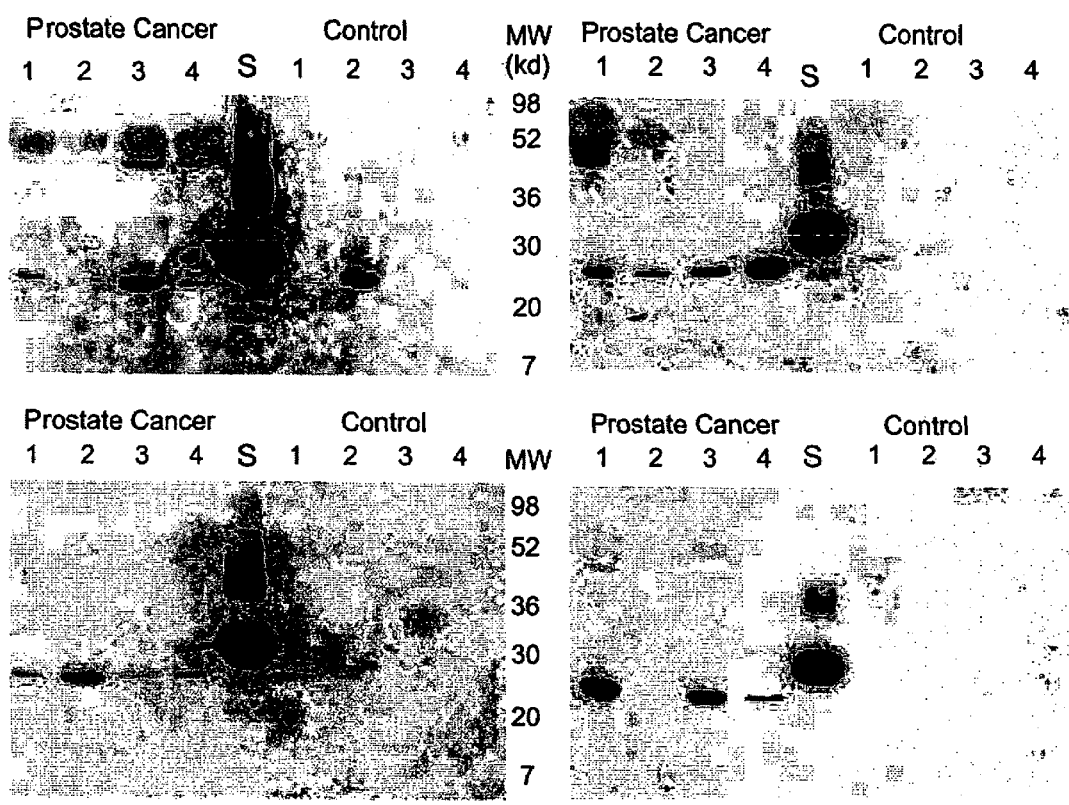
FIG. 1. Detection of cav-1 in $HDL_3$ fraction of serum. Serum samples from men with or without prostate cancer were screened by western blot. The amount of the $HDL_3$ fraction equivalent to 50 µl of serum was loaded in each lane. S: purified cav-1-V5-His protein standard (0.1 µg)

The present invention arises from the development of a specific and sensitive immunoassay for the measurement of serum cav-1 and the preliminary evaluation of its potential to discriminate men with or without prostate cancer. Importantly, the detection of secreted cav-1 in patient sera has a significant potential for clinical utility. Since unlike PSA, secreted cav-1 is associated with malignant properties of prostate cancer cells, serum cav-1 is contemplated to have unique diagnostic/prognostic capacity. The preliminary observation that cav-1 is detected in the $HDL_3$ fraction of serum samples of patients with prostate cancer (Tahir et al., 2001) is consistent with the view that $HDL_3$ is an acceptor of excess cholesterol in the plasma membrane. It is also consistent with previous studies showing that caveolae are a major site of cholesterol efflux from cells and that cav-1 mediates the intracellular movement of cholesterol (Fielding, C. J. and Fielding, P. E. Intracellular cholesterol transport. J Lipid Res, 38: 1503-1521, 1997). The present disclosure further raises the possibility that cav-1 can associate with cholesterol in the context of a serum lipoprotein particle. A previous study reported that normal human serum does not contain cav-1 based on western blotting analysis of the HDL fraction of human serum (Liu, P., Li, W. P., Machleidt, T., and Anderson, R. G. Identification of caveolin-1 in lipoprotein particles secreted by exocrine cells. Nat Cell Biol, 1: 369-375, 1999). The results disclosed herein agree with these in that the normal human serum level of cav-1 is very low to undetectable. However, based on western blot analysis (FIG. 1) levels of cav-1 in prostate cancer patients are higher than those in controls. This result was confirmed by analysis of 102 prostate cancer patient sera and 81 control sera using an immunoassay for the measurement of cav-1. Significantly higher levels of cav-1 were detected in the patient sera than the control sera (p=0.0446 Mann-Whitney test).

The direct sandwich immunoassay was developed using two polyclonal antibodies for cav-1. The HRP-conjugated detection antibody, showed a remarkable specificity to detect serum, plasma and tissue derived cav-1 as well as a recombinant C-terminal His-tagged cav-1 with minimal non specific background. Monoclonal antibodies for cav-1 that are commercially available were tested but a consistently low signal was detected using cav-1 positive sera. Some monoclonal antibodies also failed to detect the recombinant His-tagged cav-1, potentially due to a conformational change in the modified protein. A common problem encountered using polyclonal antibodies as reagents in immunoassays is that different batches of antibodies may vary markedly in their specificity and affinity for the antigen. In the assay system reported herein, this problem was overcome by extensive pre-testing and comparing any new batch or lot of antibody with the previous batch; only lots that differed by less that 5% from the original lot were used.

The use of pooled serum in the assay for the calibrator with its composition similar to the patient's sera in terms of cav-1 protein integrity in serum likely improves the accuracy of the assay, in that it should guarantee that the binding affinity between the antibody and the calibrator is the same as that between the sample analyte and antibody. The use of inappropriate calibrators in many early PSA immunoassay protocols for example contributed to disagreement among assays of PSA values produced on the same specimens (Wu, J. T. Assay for prostate specific antigen (PSA): problems and possible solutions. J Clin Lab Anal, 8: 51-62, 1994).

The cav-1 serum assay disclosed herein is contemplated to be a useful clinical tool in various applications, including but not limited to its use in arriving at a prognosis before or after prostatectomy or radiation therapy for clinically localized disease. Therefore, the sensitivity of the assay is a major consideration and the capability to detect low levels of cav-1 (below 1.0 ng/ml) is highly desirable. In general the sensitivity of an ELISA is largely determined by the affinity between the antibody and the analyte. However several other assay parameters can be optimized to improve assay sensitivity such as total reaction volume, sample concentration, diluent composition, incubation time between the coated antibody and the analyte, and between the antibody-bound analyte and the secondary or detecting antibody. The inventor has found that the use of 0.5% v/v Tween in the incubation buffer improved the sensitivity of the assay considerably; this may be due to increased solubility of serum cav-1 without affecting the binding capacity or the dissociation of the coating antibody from the microplate. Tween concentrations higher than 0.5% v/v resulted in reduced assay sensitivity.

The results that serum cav-1 levels in BPH patients were significantly lower than the prostate cancer patients', and that the BPH serum levels were not significantly different with the controls, clearly indicate that serum cav-1 is expected to be a valuable tool to discriminate between BPH and prostate cancer patients. A close examination of the cav-1 serum levels of the BPH group showed a relatively large sample to sample variation with about 6.5% of the patients having cav-1 values above 10 ng/ml. No clear explanation has been found for this observed high cav-1. However, it is conceivable that some of these patients harbored prostate cancer that was not clinically detectable at the time of examination. Unfortunately, clinical follow-up information on these patients is not available.

The correlation analysis of serum cav-1 levels with pathological parameters associated with prostate cancer did not reveal any significant associations. In previous studies the inventor has demonstrated that cav-1 expression was focally positive in primary tumors yet the percentage of cav-1 positive cells increased to nearly 40% in androgen insensitive disease. As these results indicate that an increase in cellular cav-1 is associated with virulent disease a failure to demonstrate positive correlations with pathological markers of progression was not unexpected for this specific cohort of prostate cancer specimens. The clinical and pathological data of this group of patients indicate that the majority of the patients are in an early phase of the disease with relatively low Gleason grades, seminal vascular invasion, or positive margins. The median PSA level of this group was relatively low, 5.55 ng/ml.

Described herein is the first development of a direct sandwich ELISA method for the measurement of serum cav-1 using two polyclonal antibodies, and a purified recombinant cav-1 protein as a standard. This method is highly sensitive, specific and reproducible for the detection of serum cav-1. The median serum cav-1 levels in the prostate cancer patient group were significantly higher than controls or BPH, suggesting that cav-1 in serum could be an important biomarker for prostate cancer diagnosis/prognosis and progression. Furthermore, disclosed herein is a use of detection of serum caveolin levels as a clear distinction between BPH and prostate cancer patients.

The following example is included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

Materials and Methods

Reagents. All general laboratory reagents were purchased from Sigma or BioRad unless otherwise stated. Protein concentrations were determined by the Bradford method (Bradford, M. M. Anal Biochem, 72: 248-254, 1976), using bovine serum albumin (BSA) as a calibrator (Bio-Rad protein assay; Bio-Rad Laboratories).

Expression and Purification of Cav-1 Calibrator. A plasmid, termed phcavV5His, was constructed to express the human cav-1 cDNA as a fusion protein with a V5 and 6X histidine tag. The human cav-1 cDNA was previously isolated from a cDNA library prepared from the human prostate cancer cell line PC-3. This cDNA is completely homologous with the cDNA for cav-1 in GenBank (NM 001753). The cDNA was amplified from a stock plasmid using oligonucleotide primers designed to add the restriction site EcoRI to the 5' end of the cDNA and XhoI to the 3' end of the cDNA. The sequence was carefully chosen to allow insertion into the plasmid pcDNA6/V5-HisB (Invitrogen) that was cleaved with EcoRI and XhoI. The insert was predicted to generate an in frame fusion of the V5 epitope and six histidine amino acids at the C-terminus of the expressed human cav-1 protein. The resultant plasmid was sequenced using as sequencing primers the T7 primer (on the 5' side polylinker of the hcav-1 insert) and a primer in the BGHpA region on the 3' side. The sequence and translation of the sequence confirmed that the correct fusion protein would be expressed.

The plasmid phcavV5His was transfected into 293 PE cells with Lipofectamine Plus reagent (Invitrogen) according to manufacturer instructions. The cells were collected 48 hr after transfection into centrifuge tubes and the medium was decanted, and washed twice with ice cold PBS. The washed cells were frozen and kept at −85° C. The cells from six 15 cm plates were frozen and thawed twice and suspended in 12 ml of ice cold Tris-HCl buffer (50 mM, pH 8.5 at 4° C.) containing 5 mM 2-mercaptoethanol, 1 mM phenylmethylsulfonylflouride, 20 µg/ml leupeptin, 20 µg/ml aprotenin and 1 mM Na3VO4. The suspension was sonicated until 80% of the cells were lysed. The sonicate was centrifuged at 10,000×g 20 min at 4° C. and the supernatant collected. The hcav-1V5His protein was further purified by affinity chromatography using Ni-NTA resin (Qiagen). Briefly, the column containing 6 ml of 50% slurry Ni-NTA resin was equilibrated with buffer A (20 mM Tris-HCl, pH 8.5 at 4° C., 100 mM KCl, 5 mM 2-mercaptoethanol, 10% v/v glycerol and 20 mM imidazole). The crude supernatant was loaded on the column and kept for 20 min at 4° C. The column was then washed with 10 volumes of Buffer A at a flow rate of 0.5 ml/min, followed by a wash with 2 volumes of buffer B (20 mM Tris-HCl, pH 8.5 at 4° C., 1 M KCl, 5 mM 2-mercaptoethanol, 10% v/v glycerol). The column was washed again with 2 volumes of Buffer A. The bound cav-1-V5-His was eluted with Buffer C (20 mM Tris-HCl, pH 8.5 at 4° C., 100 mM KCl, 5 mM 2-mercaptoethanol, 10% v/v glycerol and 100 mM imidazole). The eluted fraction was concentrated using Centriprep YM-10 centrifuge ultrafiltration apparatus (Amicon). Aliquots from each step of the preparation of the hcav-1V5His were analyzed by western blotting using rabbit polyclonal cav-1 antibody (Santa Cruz BioTechnology) and V5-HRP conjugated antibody (Invitrogen); the purified cav-1-V5-His had an electrophoretic mobility slightly slower than the cav-1 from cell lysates of the human prostate cancer cell lines DU145 or PC3. The purified protein concentration was measured by silver staining (Bio-Rad) a known volume of the preparation separated on SDS-PAGE and comparison to a standard curve plotted from the band intensity scanned using NucleoVision software (Nucleo Tech Corp) of at least three different concentrations of BSA standard (Pierce).

Western Blot Analysis. Serum lipoproteins were separated into lipoprotein subfractions by KBr density gradient ultracentrifugation following a modified method of Redgrave (Redgrave, T. G., Roberts, D. C., and West, C. E. Anal Biochem, 65: 42-49, 1975). Serum $HDL_3$ factions collected from 1 ml serum, were delipidated, dialyzed and freeze-dried. The powder was re-dissolved in 0.2 ml of 10 mM decyl sodium sulfate in PBS, and 10 µl of each sample, or calibrator were mixed with SDS sample loading buffer, boiled for 5 min and separated by 12% SDS-PAGE. The gel was transferred electrophoretically to a nitrocellulose membrane, and blotted with rabbit polyclonal cav-1 antibody (Santa Cruz Biotechnology) over night at 4° C., with shaking. After incubation with horseradish peroxidase-conjugated secondary antibodies (ICN Biochemicals Inc), the binding was detected by enhanced chemiluminescence with Super Signal (Pierce).

Protocol for Serum Cav-1 Assay. Two commercial affinity purified polyclonal rabbit cav-1 antibodies were chosen for a direct sandwich ELISA based on results in a direct ELISA assay using recombinant His tagged cav-1. The capture cav-1 antibody used was generated from human recombinant cav-1 (Transduction Laboratories), and the detection antibody was HRP conjugated rabbit polyclonal antibody raised against a peptide mapping at the amino terminus of human cav-1 (Santa Cruz Biotechnology). Costar microplate wells were coated with 100 µl of cav-1 antibody (5 mg/l) in carbonate buffer (pH 9.6) and incubated overnight at 4° C. The wells were then blocked with 200 µl of tris-buffered saline (TBS) containing 1.5% w/v BSA and 0.05% v/v Tween-20 for 2 h at RT, and were washed three times with TBS. Serum samples, calibrators and controls were added to the wells and incubated for 2 h at RT. All samples consisted of 50 µl aliquots diluted with 50 µl of TBS containing 0.5% v/v Tween-20. The wells were washed 4 times with 200 µl of TBS, and 100 µl of HRP-conjugated cav-1 (Santa Cruz Biotechnology) antibody diluted 1:200 in TBS containing 1.5% w/v BSA, 0.05% v/v Tween-20 were added. After incubation for 90 min at RT the wells were washed 4 times with TBS, and 100 µl of 3,3',5,5'-tetramethylbenzidine substrate solution (Sigma) were added and incubated for 20 min at RT. The reaction was stopped by adding 50 µl of 2N H2SO4, and the absorbency was read at 450 nm with a microplate reader (SLT SPECTRA, SLT Lab instruments).

Sample Specimens. Serum cav-1 was measured in three groups of subjects 50-70 years of age. The control group consisted of sera taken from 81 men (age median, 59.5 years) with normal digital rectal examinations and serum PSA levels 1.5 ng/ml or below over a period of two years. The BPH group consisted of 107 men (age median, 61.1 years) with clinical benign prostatic hyperplasia. The PSA value for only a limited number of these BPH patients were available at the time of clinical diagnosis. A group of 102 men (age median 60.8 years) with clinically localized prostate cancer, had serum samples collected pre-radical prostatectomy. The patients in this group had a median PSA level of 5.5 ng/m, (range 0.5-48.7), a relatively low percentage of extracapsular extension (33.7%), seminal vesicle invasion (4.9%), and positive margins (14.7%). The patients in this group also had negative lymph nodes. The sera were frozen at −85° C. until the day of analyses. Statistical analysis were performed using SPSS 11.0 statistical software (SPSS, Inc., Chicago, Ill.).

Determination of Optimal Antibody Concentration. The working concentrations of the antibodies were determined by chessboard titration (Crowther, J. R. The ELISA guidebook. In: Methods in molecular biology, Vol. 149, pp. 83-115. Totowa, N.J.: Humana Press, 2001) of both capture and detection antibody using constant concentration of recombinant cav-1-V5-His tagged protein. This process involves the dilution of the two antibody solutions against each other to examine the activities inherent at all the resulting combinations.

Calibrators, Controls, and Standard Curve. Calibrators were prepared by mixing a known quantity of purified recombinant cav-1-V5-His with the serum of a normal young male that has an undetectable basal level of cav-1. This stock standard and samples of the zero control serum were aliquoted and stored at −85° C. On the day of analysis a standard curve was constructed by measuring the absorbency of a serially diluted stock standard using the zero control serum as a diluent. All measurements of standards, positive controls and unknown sera were done in triplicates and the average was taken as a final reading. Three positive control sera (high, medium, and low) were identified and subsequently a large volume of the corresponding serum was aliquoted and stored at −85° C.

Since the assay uses commercially available coating and detection antibodies batches of antibody were carefully selected. A sample of the previous lot was routinely maintained and tested in comparison to a new lot to be purchased. The new lot was tested using three concentrations of the standard His-tagged cav-1 preparation and the three positive serum controls (high, medium, and low). Only lots that had absorbency readings that did not differ by more than 5% from the previous lot of antibody were selected.

Specificity. The assay specificity was tested using protein lysates from three cell lines with known cav-1 content based on western blotting. The specificity of the assay was also tested by competitive inhibition using a synthetic peptide (N-20) that specifically binds and blocks the detection antibody (Santa Cruz HRP-cav-1 antibody). The peptide was incubated with the antibody for 30 minutes at RT prior to addition to the wells.

Analytical Validation. The sensitivity of the assay, (i.e., the lowest detectable cav-1 concentration that could be distinguished from zero using statistical criteria) was calculated as the mean absorbency value of triplicate measurements of the zero standard plus three times the standard deviation. The concentration in ng/ml was calculated from the slope of the standard curve.

The intra-assay variance was determined for four serum samples with different levels (high, medium, low and very low) of serum cav-1 to determine the precision of the assay. The samples were assayed in 8 replicates. The inter-assay imprecision was determined in triplicates for four (high, medium, low and very low) cav-1 level serum samples measured on 8 subsequent independent assays.

Analytical recovery was measured by two methods. In the first, three serum samples with known concentration of cav-1 (high, medium, and low), and a known serum with an undetectable level of cav-1 as diluent was used. The serum samples and their dilutions were assayed in triplicate and the recovery calculated. In the second method for determining recovery we used three dilutions of a pre-determined concentration of recombinant cav-1 added to a control serum with undetectable cav-1. The samples were assayed in triplicate and the recovery was calculated by dividing the measured cav-1 concentration by the calculated cav-1 concentration.

Comparison of Serum and Plasma Cav-1. Three dilutions of cav-1 calibrator were made in either serum or plasma from two healthy control individuals with previously determined undetectable serum cav-1. The standard immunoassay was performed in triplicate and the mean cav-1 levels were compared. In addition we compared cav-1 concentrations in the serum and plasma of two prostate cancer patients known to have elevated cav-1 levels.

Results

Detection of Cav-1 in $HDL_3$ Fraction of Serum. Based on previous results indicating secretion of cav-1 by prostate cancer cells in vitro, serum samples from men with or without prostate cancer were screened for the presence of cav-1 by western blotting. The sera were fractionated by KBr density gradient ultracentrifugation, and a quantity of the $HDL_3$ fraction equivalent to 50 µl of serum was loaded. The band corresponding to cav-1 that migrates with an apparent molecular weight of 22-24 kd was detected in 14 out 16 prostate cancer samples while only 4 out of 16 samples of the control showed detectable level bands (FIG. 1). The standard recombinant purified cav-1 with a V5-6X-His tag migrated somewhat slower than the authentic cav-1.

Figure 2:
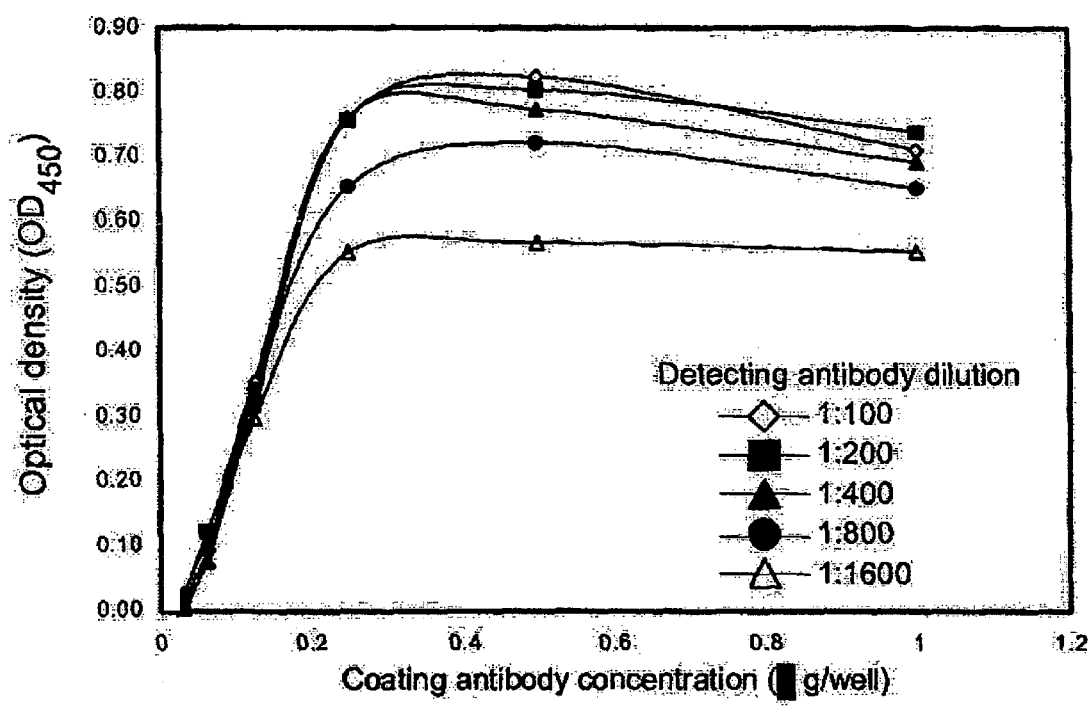
FIG. 2. Effect of coating antibody and detection antibody concentrations on sensitivity. The coating antibody was serially diluted in carbonate buffer, and the detection antibody was serially diluted in TBS blocking buffer. Each data point is the mean of three determinations. Coating antibody concentration of 0.5 µg/well, and a 1:200 detection antibody dilution were selected for the standard assay protocol.

Development of the Cav-1 Assay. The optimum cav-1 antibody pair was selected for the standard assay by testing a number of commercially available mouse and rabbit cav-1 antibodies employing a direct ELISA and using a known quantity of the recombinant cav-1. The antibody pair that gave the highest sensitivity with lowest background signal was then tested with different concentrations of both the capture and detection antibodies (FIG. 2). A concentration of 0.5 µg/well for coating (capture) cav-1 antibody and a dilution of 1/200 of the HRP-conjugated detection antibody (0.2 mg/ml of antibody) were selected for the standard assay. The incubation time, coating buffer, serum volume and diluting buffer selected in this immunoassay were based on experiments that revealed optimum detection sensitivity with minimal background or nonspecific signal.

Figure 3:
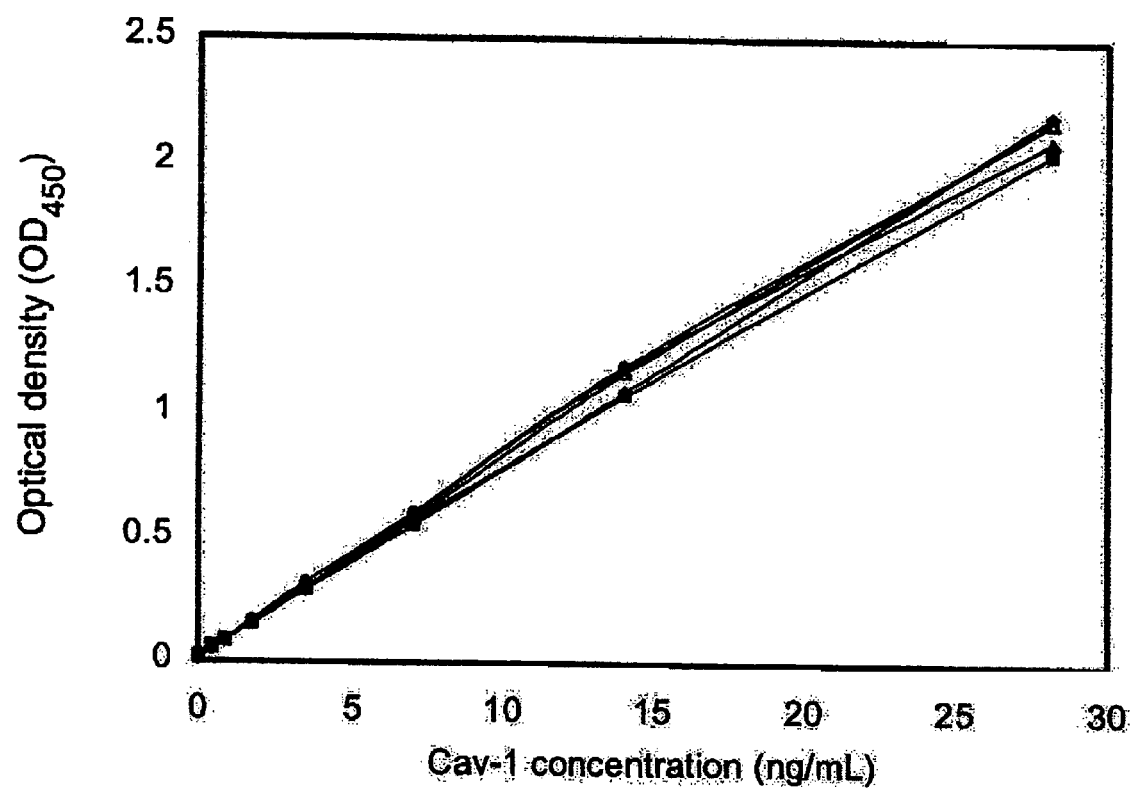
FIG. 3. Cav-1 calibration curves. Individual lines represent five independent calibration curves. Stock standard cav-1 concentration of 28.8 ng/ml in zero control serum was serially diluted using the same serum as diluent and then used in the cav-1 assay. Each data point is the mean of three determinations.

A linear standard curve was constructed using recombinant cav-1-V5-His tagged protein added to a control serum with undetectable cav-1 concentration at concentration ranges (0.0-28.2 ng/ml). The high reproducibility of the standard curve was demonstrated in five independent assays (FIG. 3).

The specificity of the assay to detect cav-1 was tested in three cell lysates, two with a high cav-1 content (human prostate cancer cell line, DU145, and mouse endothelial cell line, MS1) and one (human prostate cancer cell line, LNCaP) with undetectable cav-1 level. The optical density for LNCaP lysate was equivalent to the background and those for DU145 and MS1 were extremely high 3.62 & 2.99 respectively (Table 1). The specificity of the assay was also tested by competitive inhibition using a synthetic peptide specific to detection antibody. The peptide caused a dose dependent reduction of the signal using recombinant cav-1 as a calibrator.

Detection Limit, Precision and Recovery. The minimum detection limit of the assay was 0.017 ng/ml when calculated from the response for the zero calibrator plus 3 SD, repeated in 8 different independent assays. Inter-assay precision was determined using four different pools of serum in 8 independent assays over a period of one month using two different lots of capture antibody and one lot of HRP-conjugated antibody (CV<6.43%). The intra-assay precision was determined using four different pools of serum assayed in 8 replicates in one assay (CV<6.74%), (Table 2).

The recovery of cav-1 in a positive control serum sample was determined in three serial dilutions (1:2, 1:4, 1:8), and the median recovery was 92.7% (range, 89.55%-99.25%). Using the His-V5-cav-1 calibrator spiked into a serum with zero cav-1 concentration and serially diluted, the median recovery was 100.14% (range, 98.3-100.28%) (Table 3). It was further determined that the recovery using a positive control serum with extremely high cav-1 (126.13 ng/ml), and when this sample was diluted 10 fold the recovery was 104.95%.

Cav-1 in Plasma Samples. The cav-1 immunoassay for the measurement of cav-1 in plasma specimens showed similar sensitivity and reproducibility to that of serum using two positive control sera, as well as standard cav-1 calibrator spiked into two negative control sera and plasma samples (Table 4).

Cav-1 Levels in Prostate Cancer, BPH Patients and Controls. The serum cav-1 concentration in 81 control subjects was measured and the median was 0.324 ng/ml (range, 0.0-5.73 ng/ml). The median cav-1 concentration in the sera of the men with BPH was 0.172 ng/ml (range, 0.0-59.9 ng/ml). The serum levels in the control group were not significantly different than the BPH group (p=0.835, Mann-Whitney). Comparisons between levels of Cav-1 were made with Mann-Whitney test, which uses the number of times a value in one group precedes a value in the other group, when values are sorted in ascending order. The median cav-1 concentration in the sera of the prostate cancer patients was 0.461 ng/ml (range, 0.0-95.8 ng/ml) which was significantly higher than the control group (p=0.0446, Mann-Whitney test) or the BPH group (p=0.0317, Mann-Whitney test) (Table 5). The prostate cancer samples were also analyzed for statistical correlation of serum cav-1 levels with serum PSA and specific clinical and pathological parameters associated with these prostate cancer specimens (Gleason score, positive 16 margin status, extracapsular extension and seminal vesicle invasion), but no significant correlations were observed (Spearman Rank correlation).

TABLE 1

Specificity of the cav-1 ELISA

| cell lysate | $OD_{450\,nm}$ | cav-1 level[a] |
|---|---|---|
| Blank | 0.064 | |
| LNCaP[b] (low passage) | 0.076 | undetectable |

TABLE 1-continued

Specificity of the cav-1 ELISA

| cell lysate | OD$_{450\,nm}$ | cav-1 level[a] |
|---|---|---|
| MS1[c] | 2.99 | high |
| DU145[b] | 3.62 | high |

[a]Western blot
[b]Human prostate cancer cell line
[c]Mose endothelial cell line

TABLE 2

Precision of the cav-1 ELISA.

| | | Inter-assay | | Inter-assay | |
|---|---|---|---|---|---|
| Sample | cav-1 level | ng/ml | CV (%) | ng/ml | CV (%) |
| A | Very low | 0.4-0.48 | 6.43 | 0.25-0.285 | 6.74 |
| B | Low | 1.84-2.1 | 5.6 | 2.6-2.8 | 3.1 |
| C | Medium | 6.3-7.8 | 4.26 | 13.2-14.6 | 3.07 |
| D | High | 28.56-30.76 | 2.81 | 30.29-31.89 | 2.29 |

TABLE 3

Analytical recovery of cav-1.

| | Serum positive control | | Standard recombinant cav-1 | |
|---|---|---|---|---|
| Dilution | ng/ml | % Recovery | ng/ml | % Recovery |
| 1:2 | 8.04 | 99.25 | 14.12 | 98.3 |
| 1:4 | 4.02 | 89.55 | 7.06 | 100.14 |
| 1:8 | 2.01 | 92.7 | 3.53 | 100.28 |

TABLE 4

Comparison of cav-1 detection in serum and plasma

| | Serum Cav-1 (ng/ml) | Plasma Cav-1 (ng/ml |
|---|---|---|
| Specimen A[a] (ng/ml) | | |
| 0 | 0.0 | 0.0 |
| 3.53 | 4.15 | 4.76 |
| 7.06 | 8.83 | 9.25 |
| 14.1 | 16.7 | 16.35 |
| Specimen B[a] (ng/ml) | | |
| 0 | 0 | 0 |
| 3.53 | 4.25 | 4.84 |
| 7.06 | 9.06 | 9.19 |
| 14.1 | 16.2 | 16.29 |
| Positive control 1[b] | 17.18 | 20.97 |
| Positive control 2[b] | 4.88 | 4.46 |

[a]Different concentrations of cav-1 calibrator spiked into the serum and plasma specimens of two independent control subjects with undetectable cav-1 levels.
[b]Two independent prostate cancer patients with serum and plasma collected at the same time

TABLE 5

Statistical comparison of serum cav-1 in Control, BPH & prostate cancer patients

| Group | N | Median (ng/ml) | Range (ng/ml) | Mean Ranks*/P value vs. Control | Mean Ranks*/P value vs. Cancer |
|---|---|---|---|---|---|
| Control | 81 | 0.324 | 0.0-5.7 | — | 83 vs 99/ 0.0446 |
| BPH | 107 | 0.172 | 0.0-59.9 | 94 vs 95/ 0.8350 | 96 vs 114/ 0.0317 |
| Prostate cancer | 102 | 0.463 | 0.0-95.8 | 99 vs 83/ 0.0446 | |

*Calculated using combined, sorted and ranked two-group data

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the methods described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

1. Greenlee, R. T., Hill-Harmon, M. B., Murray, T., and Thun, M. Cancer statistics, 2001. CA Cancer J Clin, 51: 15-36, 2001.
2. Brawley, O. W., Giovannucci, E., and Kramer, B. S. Epidemiology of prostate cancer. In: S. P. Vogelzang N J, Shipley W U, Coffey D S (ed.), Comprehensive Textbook of Genitourinary Oncology, pp. 533-544. Philadelphia, Pa.: Lippincott Williams and Wilkins, 2000.
3. Stephan, C., Jung, K., Diamandis, E. P., Rittenhouse, H. G., Lein, M., and Loening, S. A. Prostate-specific antigen, its molecular forms, and other kallikrein markers for detection of prostate cancer. Urology, 59: 2-8, 2002.
4. Babaian, R. J., Camps, J. L., Frangos, D. N., Ramirez, E. I., Tenney, D. M., Hassell, J. S., and Fritsche, H. A. Monoclonal prostate-specific antigen in untreated prostate cancer. Relationship to clinical stage and grade. Cancer, 67: 2200-2206, 1991.
5. Partin, A. W., Yoo, J., Carter, H. B., Pearson, J. D., Chan, D. W., Epstein, J. I., and Walsh, P. C. The use of prostate specific antigen, clinical stage and Gleason score to predict pathological stage in men with localized prostate cancer. J Urol, 150: 110-114, 1993.
6. Ohori, M., Goad, J. R., Wheeler, T. M., Eastham, J. A., Thompson, T. C., and Scardino, P. T. Can radical prostatectomy alter the progression of poorly differentiated prostate cancer? J Urol, 152: 1843-1849, 1994. 23
7. Zietman, A. L., Edelstein, R. A., Coen, J. J., Babayan, R. K., and Krane, R. J. Radical prostatectomy for adenocarcinoma of the prostate: the influence of preoperative and pathologic findings on biochemical disease-free outcome. Urology, 43: 828-833, 1994.
8. Li, W. P., Liu, P., Pilcher, B. K., and Anderson, R. G. Cell-specific targeting of caveolin-1 to caveolae, secretory vesicles, cytoplasm or mitochondria. J Cell Sci, 114: 1397-1408, 2001.
9. Yang, G., Truong, L. D., Timme, T. L., Ren, C., Wheeler, T. M., Park, S. H., Nasu, Y., Bangma, C. H., Kattan, M. W., Scardino, P. T., and Thompson, T. C. Elevated expression of caveolin is associated with prostate and breast cancer. Clin Cancer Res, 4: 1873-1880, 1998.
10. Yang, G., Truong, L. D., Wheeler, T. M., and Thompson, T. C. Caveolin-1 expression in clinically confined human prostate cancer: a novel prognostic marker. Cancer Res, 59: 5719-5723, 1999.
11. Yang, G., Addai, J., Ittmann, M., Wheeler, T. M., and Thompson, T. C. Elevated caveolin-1 levels in African-American versus white-American prostate cancer. Clin Cancer Res, 6: 3430-3433, 2000.
12. Nasu, Y., Timme, T. L., Yang, G., Bangma, C. H., Li, L., Ren, C., Park, S. H., DeLeon, M., Wang, J., and Thompson, T. C. Suppression of caveolin expression induces androgen sensitivity in metastatic androgen-insensitive mouse prostate cancer cells. Nat Med, 4: 1062-1064, 1998.
13. Tahir, S. A., Yang, G., Ebara, S., Timme, T. L., Satoh, T., Li, L., Goltsov, A., Ittmann, M., Morrisett, J. D., and Thompson, T. C. Secreted Caveolin-1 24 Stimulates Cell Survival/Clonal Growth and Contributes to Metastasis in Androgen-insensitive Prostate Cancer. Cancer Res, 61: 3882-3885, 2001.
14. Bradford, M. M. A rapid and sensitive method for the quantitation of microgram quantities of protein utilizing the principle of protein-dye binding. Anal Biochem, 72: 248-254, 1976.
15. Redgrave, T. G., Roberts, D. C., and West, C. E. Separation of plasma lipoproteins by density-gradient ultracentrifugation. Anal Biochem, 65: 42-49, 1975.
16. Crowther, J. R. The ELISA guidebook. In: Methods in molecular biology, Vol. 149, pp. 83-115. Totowa, N.J.: Humana Press, 2001.
17. Li, L., Yang, G., Ebara, S., Satoh, T., Nasu, Y., Timme, T. L., Ren, C., Wang, J., Tahir, S. A., and Thompson, T. C. Caveolin-1 mediates testosterone-stimulated survival/clonal growth and promotes metastatic activities in prostate cancer cells. Cancer Res, 61: 4386-4392, 2001.
18. Timme, T. L., Goltsov, A., Tahir, S., Li, L., Wang, J., Ren, C., Johnston, R. N., and Thompson, T. C. Caveolin-1 is regulated by c-myc and suppresses c-mycinduced apoptosis. Oncogene, 19: 3256-3265, 2000.
19. Fidler, I. J. Critical factors in the biology of human cancer metastasis: twenty eighth G.H.A. Clowes memorial award lecture. Cancer Res, 50: 6130-6138, 1990.
20. Liu, P., Li, W. P., Machleidt, T., and Anderson, R. G. Identification of caveolin-1 in lipoprotein particles secreted by exocrine cells. Nat Cell Biol, 1: 369-375, 1999.
21. Fielding, C. J. and Fielding, P. E. Intracellular cholesterol transport. J Lipid Res, 38: 1503-1521, 1997.
22. Wu, J. T. Assay for prostate specific antigen (PSA): problems and possible solutions. J Clin Lab Anal, 8: 51-62, 1994.

The invention claimed is:

1. A method of diagnosing prostate cancer comprising detecting caveolin-1 in the serum of a subject suspected of or susceptible to developing prostate cancer, wherein a serum caveolin-1 level that is significantly higher than the serum caveolin-1 of a pool of subjects without prostate cancer is indicative of prostate cancer.

2. The method of claim 1, wherein the caveolin-1 is detected in the $HDL_3$ fraction of the serum.

3. The method of claim 1, wherein the caveolin-1 is detected by an anti-caveolin-1 antibody in an assay.

4. The method of claim 3, wherein the assay is a sandwich immunoassay.

5. The method of claim 3, wherein the antibody is a rabbit antibody.

6. The method of claim 3, wherein the antibody is a human antibody.

7. The method of claim 1, wherein the subjects without prostate cancer have benign prostatic hyperplasia.

* * * * *